United States Patent
Pearson et al.

(10) Patent No.: US 7,166,652 B2
(45) Date of Patent: Jan. 23, 2007

(54) POLYMERISABLE RESIN COMPOSITIONS FOR USE IN DENTISTRY

(75) Inventors: Gavin John Pearson, Ashamstead (GB); Jill Ann Williams, Thorpe (GB); David John Clements, Crawley Down (GB); Michael Braden, Harpenden (GB); Ray Todhunter, Kerrering (GB); Mangala Patel, Mill Hill (GB)

(73) Assignee: Denfotex Ltd., London (GB)

( * ) Notice: Subject to any disclaimer, the term of this patent is extended or adjusted under 35 U.S.C. 154(b) by 90 days.

(21) Appl. No.: 10/181,128

(22) PCT Filed: Jan. 15, 2001

(86) PCT No.: PCT/GB01/00150

§ 371 (c)(1),
(2), (4) Date: Jan. 16, 2003

(87) PCT Pub. No.: WO01/50974

PCT Pub. Date: Jul. 19, 2001

(65) Prior Publication Data

US 2003/0162864 A1    Aug. 28, 2003

(30) Foreign Application Priority Data

Jan. 14, 2000   (GB) ................... 0000882.1
Jan. 14, 2000   (GB) ................... 0000884.7
Jan. 14, 2000   (GB) ................... 0000886.2

(51) Int. Cl.
  A61K 6/083    (2006.01)
  C08K 3/40     (2006.01)
  A61C 5/00     (2006.01)
(52) U.S. Cl. .................. 523/116; 523/118; 524/494; 524/549; 433/228.1
(58) Field of Classification Search ............... 523/116, 523/118; 524/494, 549
  See application file for complete search history.

(56) References Cited

U.S. PATENT DOCUMENTS 4,966,934 A * 10/1990 Huang et al. ............... 524/315
5,739,177 A *  4/1998 Ohno et al. ................ 523/118
5,834,532 A * 11/1998 Yamamoto et al. ......... 523/118
5,971,754 A * 10/1999 Sondhi et al. ............... 433/24
6,313,192 B1 * 11/2001 Anstice et al. .............. 523/116

FOREIGN PATENT DOCUMENTS

WO    WO 98/30192    *  7/1998

* cited by examiner

*Primary Examiner*—Tae H Yoon
(74) *Attorney, Agent, or Firm*—Connolly Bove Lodge & Hutz LLP; Matthew J. Mason

(57) ABSTRACT

A polymerisable dental filling and sealing composition is provided which comprises a mixture of at least one resin containing on average at least two acrylate or methacrylate groups and a copolymerisable methacrylate or acrylate monomer, which has a low viscosity compared with said resin, the copolymerisable monomer being present in an amount such that the composition can be introduced by syringing into a cavity having a diameter of less than 1 mm.

25 Claims, No Drawings

POLYMERISABLE RESIN COMPOSITIONS FOR USE IN DENTISTRY

This invention relates to resin compositions which may be used to infill partly or wholly demineralised dentine and provide coatings to both enamel and dentine surfaces to seal them from bacterial ingress.

BACKGROUND OF THE INVENTION

Currently, resins are used as replacements for dental tissue after diseased tissue has been excised by the use of dental burs and excavators. Typical uses are restoration of teeth, cementing crowns and inlays and fixing orthodontic devices in places. They may also be used as bases and liners in conventional cavities. Further hydrophilic resin mixtures may be used to mechanically interlock with the surface of the freshly cut dentine to bind the resin to the tooth in an attempt to achieve a hermetic seal.

These resins are usually a composite of filler and a polymerisable resin based on one or more methacrylates or acrylates. The base resins used are often of high viscosity and are hydrophobic. Long chain materials are thought to reduce the shrinkage on polymerisation. The mechanical properties of the resin alone are inadequate for the restoration of conventional cavities and the filler is added to enhance the mechanical properties and impart radiopacity The filler is generally an inert glass or silica and takes no part in the setting reaction. The filler is normally coated with a silane-coupling agent to enhance the union between the glass and the resin. This coupling agent is normally a difunctional vinyl silane. Setting is achieved by free radical polymerisation of the monomer component. This may be achieved in a number of ways and is dependent on the presentation of the material. The most common presentation is a paste, which contains an α diketone and an amine reducing agent. The diketone is excited by a high intensity light of a wavelength generally between 450–480 m, and the polymerisation reaction occurs. Alternatively, the materials may be presented as two components, generally pastes. The polymerisation reaction is initiated by mixing the two pastes together. Each paste will contain either benzoyl peroxide or a tertiary amine. The combination of these two chemicals results in polymerisation of the resin.

These resins have good aesthetic properties and the addition of filler provides adequate mechanical properties for some uses. However, the nature of the setting reaction and the polymerisation shrinkage and exotherm presents problems associated with marginal leakage around the restoration. This can cause further problems as bacteria can track between the restoration and the tooth structure. This will lead to recurrent infection and further caries. Some materials, which use resin technology also, contain polyacids, which react with the filler and form a polysalt matrix. These are known as resin modified glass ionomer cements. These have the advantage that the polysalt matrix contains fluoride ions, which may be released and diffuse out from the restorative into the surrounding tooth structure and oral cavity. The presence of this polysalt matrix weakens the set material and results in a restoration, which is not as strong as ordinary resin composite. These materials are not suitable for load bearing restorations and form a stiff paste prior to setting. Further developments have utilised both dimethacrylate resins but also difunctional monomers where carboxylate groups are present, which react with water after the restoration has been placed. The main purpose of this is to provide some fluoride release while maintaining the mechanical properties of the resin composites. These still suffer from the problems of polymerisation shrinkage and exotherm.

Resin composites and their hybrids rely for retention on mechanical preparation of the enamel and for retention to dentine there is a secondary material applied as a dentine adhesive prior to the application of the composite. The materials are in the form of a paste in order to facilitate the retention of the material in a wide cavity. Alternative materials for restoration of teeth are the glass ionomer cements, which set primarily by an acid base reaction between the fluoro-alumino-silicate glass and the polyacid such as poly acrylic acid. Again, these materials are required to be a stiff paste to aid insertion and retention within a conventional cavity. Their main benefit is adhesion to both enamel and dentine and also the sustained release of fluoride over periods in excess of four years.

SUMMARY OF THE INVENTION

The present invention addresses the problem of providing resin compositions of lower viscosity, which may be used as a means of infusing infected dentine which has been demineralised and which may be used to coat dentine surfaces to provide a seal. Prior to infusing the dentine, bacteria may be killed using methods as described in our co-pending PCT patent applications Nos. WO 00/74587 and WO 00/62701, and the residual material that is partly demineralised dentine containing partly or completely denatured collagen filled with resin solutions.

Difficulties are often encountered in conventional dentistry when sealing cavities, including pits and fissures, in the surface of a tooth in ensuring that the restoration or sealant material completely fills and seals the cavity. In part, this is because conventional materials have a pasty character because of the nature and amounts of filler which they contain. A high filler loading has been thought to be essential for satisfactory results, particularly where the repaired tooth surface includes an occlusal surface.

According to one aspect of the present invention there is provided a polymerisable dental filling and sealing composition which comprises a mixture of at least one resin containing on average at least two acrylate or methacrylate groups and a copolymerisable methacrylate or acrylate monomer, which has a low viscosity compared with said resin, the copolymerisable monomer being present in an amount such that the composition can be introduced by syringing into a cavity having a diameter of less than 1 mm.

In the course of development of this invention, experiments have been carried out on a number of monomer mixes which may be used and it has been found that good results may be obtained by using a range of resin mixes containing both methacrylate and dimethacrylate monomers and resins. These include urethane dimethacrylate (UDMA); bisphenol-A-glycidyl dimethacrylate (BisGMA); tetrahydro-furfuryl methacrylate (THFMA) and hydroxyethyl methacrylate (HEMA). Other suitable materials include methacrylates, dimethacrylates, ormocers and spiroorthocarbonates. The mixture may contain other heterocyclic monomers such as tetrahydropyranyl methacrylate, tetrahydropyran-2-ylmethyl methacrylate and isobornyl methacrylate. All these monomers are used in a variety of material and for a variety of dental applications. BisGMA and UDMA are the main constituents in composite resin restorative materials and have been cited in a number of patents and THFMA has been cited for use as a means for tissue repair and as a temporary crown and bridge resin, and in the construction of dentures and dental bridges and crowns—see, for example, WO 93/09819; WO 81/02022 and U.S. Pat. No. 4,264,489. Further additions of hydrophilic monomers to improve wettability such as HEMA may also be used.

The composition may optionally contain some inert material to vary the viscosity to the appropriate level for the proposed use and to improve the strength. This may be in the form of an amorphous fumed silica, colloidal silica particle size range within 400–10 nm or by use of pre-polymerised particles of the resin mixture or using flake glass (e.g. Asatulin).

Flake glass is a particularly preferred filler since sufficient flake glass can be added to the resin compositions of this invention to provide an occlusal surface without increasing the viscosity above a level which would preclude syringing. One suitable commercially available flake glass filler is manufactured by Corrocoat Limited, Forster Street, Leeds, LS10 1PW, UK. This filler material is manufactured from 'C' glass and modified glass formulations as thin, high aspect ratio flakes, preferably having a particle size from about 0.5 to 10 µm and an aspect ratio of from about 5:1 to 10:1. The flake glass is preferably added in an amount which improves the biaxial strength of the cured resin by between one-third and one-half. The filler should not be reactive with the resin components and additional ingredients which leach components of the glass should be avoided. The inert filler, preferably flake glass, should preferably be employed in an amount of less than 20% of the composition, more preferably less than 15%, e.g. between about 5 to 15%, especially 10 to 15%.

The system may be polymerised by either ultraviolet or visible light or by cold cure initiators. Preferred visible light induced initiators include camphoroquinone and an amine, diaryliodonium simple or metal complex salts, chromophore substituted halomethyl-s-triazines and halomethyl oxadioazoles.

Preferred UV light induced polymerisation initiators include diketones such as benzoyl and benzoin and acrylions and acrylion ethers.

Auto or cold curing initiators which are not dependent on exposure to light or heat may also be used and include benzoyl peroxide and a tertiary amine activator such as N,N-dimethyl-p-toluidine.

These initiator components should be present in suitable proportions to provide the desired rate and extent of conversion of the monomer to the polymeric form. Typically, they may be found in concentrations ranging from 0.1% to 10% of the monomer mixture. The more preferred concentrations are in the region of 0.5% to 4%.

The composition may fuirther include fluoride containing salts as described in U.S. Pat. No. 5,718,924, or the addition of amine fluorides.

Various other additives may also be included in the composition such as antioxidants, stabilisers such as UV inhibitors and polymerisation inhibitor pigments. Other therapeutic agents such as antibiotics and corticosteroids and other medicinal agents may also be incorporated.

The resin mixture may be used in the reinforcement of demineralised dentine and in the sealing of the walls of root canals following the debridement and killing of bacteria in the dentine.

The materials will be in the form of a fluid monomer mix having a viscosity range between 0.33 and 1340 centipoise at a temperature of 37° C. These mixtures may then be syringed into the lesion prior to initiation of set. This may be achieved by exposing the material to a light source operating at the appropriate wavelength such that the material may set within a clinically acceptable time up to 3 minutes after placement. Alternatively, the material will be presented as a two liquid system which may be mixed and then syringed into the lesion. Activation of the setting reaction is achieved by the mixing of the two monomer phases. Setting is achieved using autopolymerisation. Setting will be within acceptable clinical times, of the order of ten minutes maximum.

The use of a monomer mixture has certain advantages. The mixture has a low shrinkage and good biological compatibility because of the presence of THFMA and has a viscosity, which permits the syringing of the material into semi-solid structures.

The low viscosity resin compositions of this invention are especially useful in sealing root canals after cleaning and sterilising the root canal as described in WO 00/74587. In this embodiment of the invention, it is preferred to introduce an unfilled resin sealant composition into the canal but not to fill the canal completely. Curing of the composition can be initiated by light directed down the canal from a source within the patient's mouth. However, it is preferred to employ an optical fibre having an isotropic tip within the canal of the kind described and illustrated in WO 00/74587. As the resin compositions are anaerobic curing systems, the top surface of the cured resin within the canal will have a 'cheesy', partially cured condition. The remainder of the canal can then be filled with a resin composition containing sufficient inert filler to provide an upper surface which provides a biting surface. The filled resin can then be cured, e.g. with light initiation and this will bond to the cheesy surface of the unfilled, cured resin composition (or composition containing a low level of filler).

The reinforcement of the resin with filler is preferably achieved by the use of pre-treated high aspect ratio glasses. These glass particles may be coated with a silane coupling agent to improve the wettability of the glass surface prior to incorporation within the resin. Methods of silane coupling are described in a number of texts. The basic method is to prepare a slurry of the silanizing agent, e.g. ý-methacryloxypropyltrimethoxysilane, [A 174 Union Carbide]. The silane is placed in a 99.9% ethanol solvent. The glass/silane/ethanol/slurry is stirred for an hour and the solvent then evaporated. The glass is then dried, maximising the condensation of the silane and decaked. The glasses may be produced using the method described in European Patent No. 0289240B1. Particles of thicknesses of the order of 0.5–10 µm and aspect ratio of 5:1 and 10:1 have been evaluated with glass formulations as follows:

| | $SiO_2$ | $Al_2O_3$ | BaO | SrO | F | $B_2O_3$ | ZnO | CaO | $N_2O$ | $P_2O_5$ |
|---|---|---|---|---|---|---|---|---|---|---|
| A | 40 | 29 | 0.39 | 19 | 6 | | | 0.64 | 2.5 | 4.8 |
| B | 50 | 10 | 30 | | | 10 | | | | |
| C | 30 | 20 | | 20 | 15 | | 10 | | 2.5 | 2.5 |
| D | 30 | 24 | 0.5 | 29 | 13 | | | | 2.4 | 6 |

The addition of the flake glass increases the biaxial strength of the resin by between one third and one half depending on the volume of glass included in the resin.

The resin compositions can be regarded as dentine substitute materials and are designed to achieve three distinct actions:

1) infiltrate the remaining softened and denatured dentine after the bacteria has been killed, using the techniques described in WO 00/74587;

2) reinforce the weakened dentine and form a dentine substitute;

3) with the addition of fillers seal the access cavity and withstand occlusal load.

The proposed means of achieving this can be divided into four phases. For each phase a specific material or combination of materials may be used. The combination of the materials may reduce the number of phases but the four distinct phases will be described, with the appropriate single material for each.

1) Conditioning of the Dentine After Application of PDT (Photodynamic Therapy)—see WO 00/74587 and WO 00/62701.

Initially, the dentine after killing the bacteria contains a large proportion of water and partly denatured collagen. In order to infiltrate this structure a conditioner is needed. This may be materials such as citric acid, polyacrylic acid, polymaleic acid, ferric chloride and ferric oxalate. These have been documented and are known for their ability to maintain the dentine in an undehydrated form [Hybridization of dental hard tissue, Chapters 3 & 4, Nakabayashi and Pashly Quintessence Publications, 1998, Tokyo]. For present purposes, we have found that a combination of polyacrylic acid and ferric chloride produces the best dentine structure which may be infused with a primer. This should be applied for a period of between 10–60 seconds, preferably for 30 seconds. The liquid would be injected into the root canal or other cavity for the requisite time and then aspirated with a syringe removing the bulk of the material.

2) Priming the Dentine

Once the dentine has been conditioned, a solution of resins will be injected into the cavity to infiltrate the dentine and be polymerised in situ. The resin system may be either a mixture of UDMA, BisGMA, HEMA and THFMA or other methacrylates or THFMA and UDMA in an acetone or other volatile material.

Our preferred materials for both systems are set out below:

Two conditioners have been examined. These are solutions containing:

[X]—1 Molar [25%] Polyacrylic acid

[Y]—1 Molar [25%] Polyacrylic acid and 1% Ferric Chloride

These are applied first followed by a low viscosity primer. Primers contain the following:

Of the combinations used, the best results as infiltration of the carious dentine were obtained with the following combinations. [Assessment was by confocal microscopy scanning, electron microscopy].

| Conditioner | Primer | Result |
|---|---|---|
| Y | E | Resin well adapted: bridges of resin into tooth structure; primer well down into tubules |
| Y | C | Resin well bonded; tubules well filled |
| Y | A/B | Resin appears well adapted |
| X | E | Resin difficult to remove but few resin tags |
| X | C | Resin pulls off in one piece; no resin tags |
| X | A/B | Resin peels away in one lump; no tags visible |

The mode of application of the primer is by injection into the cavity of a small unit dose of about 0.2 ml of resin. If the acetone based material is used then about 30 seconds are required for this to evaporate.

The primer may then be polymerised either using a conventional curing unit or by using the isotropic emitter which is placed within the cavity and cured in situ. Alternatively, the bulk dentine substitute may be applied to fill the dentine cavity and the primer and bulk substitute cured together.

3) Bulk Dentine Substitute

The bulk dentine substitute is a combination of UDMA.BisGMA and THFMA. Additives such as HEMA and various fluoride additions may be added. This fills the bulk of the cavity and provides a seal up the tunnel wall. In very small access cavities, it may provide the complete seal for the whole cavity.

4) Reinforced Bulk Dentine Substitute

This is used where the access cavity is liable to be subjected to occlusal load. The bulk resin may be reinforced by the addition of various levels of radiopaque glass filler. This is in the form of high aspect ratio glass fragments which will act as crack stoppers.

The advantage of these systems is that they are all based on a similar resin composition. All these compositions cure by free radical polymerisation. The polymerisation reaction is anaerobic in nature and there is air inhibition at the surface during each polymerisation stage. This has an advantage that as each addition is made, the increments bond together forming a continuum.

|   | THFMA | UDMA | HEMA | BisGMA | Camp | DMPT | BP |
|---|---|---|---|---|---|---|---|
| A | 48.2 | 33.0 |  | 16.2 |  |  |  |
| B | 49.6 | 49.6 |  |  |  |  | 0.66 |
| C | 44.5 | 37.8 | 9.0 | 6.6 | 0.54 | 0.73 |  |
| D | 44.8 | 41.8 |  | 7.1 | 0.59 | 0.79 |  |
| E | 4.9 | 4.9 |  |  | 0.05 | 0.07 | 90 acetone |

THFMA: tetrahydrofurfurylmethacrylate
UDMA: urethane dimethacrylate
HEMA: hydroxyethyl methacrylate
BisGMA: bisphenol A glycidyl dimethacrylate
Camp: Camphorquinone
DMPT: dimethyl p toluidine
[A] and [B] were used together in a 50/50 mixture.

Details of Bulk Resin

A range of mixtures have been evaluated and are appended below: All components as percentages. Biaxial strength in Mpa {columns 7 & 8}

| | Bis G | UDMA | THFMA | Addit 1 | Addit 2 | 1 day | 3 months |
|---|---|---|---|---|---|---|---|
| A | 0 | 50 | 50 | | | 84 | 107 |
| B | 33 | 17 | 50 | | | 118 | 131 |
| C | 50 | 0 | 50 | | | 152 | 100 |
| D | 17 | 33 | 50 | | | 177 | 108 |
| E | 17 | 33 | 50 | | | 156 | |
| F | 17 | 33 | 50 | 2% af | | 102 [40–166] | |
| G | 17 | 33 | 50 | 2% af | 2.1% PMA | 135 [98–152] | |
| H | 17 | 33 | 50 | 2% af | 2% HEMA | 102 [62–144] | 95 |
| J | 17 | 33 | 50 | 2% af | 2% PAA solid | 47 | |
| K | 17 | 33 | 50 | 2% af | 2% PAA sol/gel | 49 | | af = Amine fluoride

The best values were obtained with the BisGMA 17.6%; UDMA 33%; THFMA 50%.

| Modulus for this mixture is 2.28 Gpa and with additions modulus drops | |
|---|---|
| | Gpa |
| Mixture + amine fluoride 2% | 1.71 |
| Mixture + amine fluoride 2% + 2% HEMA | 1.71 |

| Volumetric shrinkage % [wet] | | | | | | |
|---|---|---|---|---|---|---|
| | 4 hrs | 2d | 6d | 14d | 21d | 42d | 66d |
| Resin mixture [x] | 1.09 | | 2.79 | | 2.95 | 3.48 | |
| [x] 2% af | 1.87 | 2.74 | 3.77 | 4.23 | 4.60 | 5.26 |
| [x] 2% af/2% HEMA | 1.42 | 1.97 | 2.86 | 4.42 | 4.15 | |

| Hardness {Wallace} μm indentation | | | | |
|---|---|---|---|---|
| | 4 hrs | 2d | 7d | 21d | 42d |
| Resin mix | | | 78 | 62 | 64 |
| 2% amine f | 137 | | 40 | 61 | 52 |
| 2% af/ HEMA | 190 | | | 62 | 71 |
| 2% af/PMA | 132 | 86 | | | |

The preferred base resin composition is the BisGMA 17.6; UDMA 32.4; THFMA50 mixture with Camphoroquinone and DMPT as the activator system. HEMA and other additives provide good wettability and also in respect of fluoride release with the addition of amine fluoride.

Cumulative fluoride release over periods of 205 days equivalent to 6.7 ppm cumulative. Radiopacity of the resin may be achieved by adding the iodinated methacrylate monomer described by Davey K and Braden M in European Patent on radiopaque denture base material.

For the applications described, the viscosities of all the resin systems used should be within the range 0.33–1340 centipoise and more preferably between 0.33 and 250 centipoise.

The following examples indicate the properties of some of these resin mixes.

A preferred composition comprises THFMA, UDMA and BisGMA in the proportions of about 40 to 60 weight percent THFMA (e.g. about 50 weight percent), about 25 to 35 weight percent UDMA (e.g. about 33 weight percent) and about 12 to 18 weight percent of BisGMA (e.g. about 16 weight percent). Typically, an initiator is present in an amount of about 1 to 2% by weight and the composition may also include a fluoride salt, e.g. barium or strontium fluoride in an amount of about 1 to 5%, e.g. about 2%.

EXAMPLE 1

Resin mix BisGMA:UDMA:THFMA 16:33:50 2% initiators added.

Biaxial flexural strength Mpa

| 24 hours | 1 week | 1 month | 3 months |
|---|---|---|---|
| 110[80–179] Second series 178, 134, 108, 118 70: Mean 122 | 140{90–180} | 150{106–178} | 147{140–220} |

Water sorption at saturation 3.5% Solubility 0.36% at equilibrium

EXAMPLE 2

Basic resin with additions

| Addition | Flexural Strength (Mpa) | Mean | Comment |
|---|---|---|---|
| 2% Olaflur | 166, 149, 135, 147, 104, 94 | 132 | Dependent on thickness |
| 2% Olaflur | 40, 89, 110, 123, 129 | 98 | Slight thickness dependency |
| 2% Olaflur plus 2% HEMA | 62, 83, 93, 126, 144 | 102 | Slight thickness dependency |

All specimens were polymerised by light at a wavelength of between 450–470 nm using a conventional light curing unit. Patch curing was carried out to ensure adequate polymerisation.

The invention claimed is:
1. A polymerisable dental filling and sealing composition which comprises a mixture of (i) at least one resin containing on average at least two acrylate or methacrylate groups; and (ii) at least 40 wt % of a copolymerisable methacrylate wherein the polymerisable dental filling and sealing composition has a viscosity of less than 1340 centipoise at 37° C.; and which further comprises a filler which is not reactive with the resin components and wherein said conolymerisable methacrylate is tetrahydro-furfuryl methacrylate (THFMA).

2. A composition as claimed in claim 1 which has a viscosity of between 0.33 and 1340 centipoise at 37° C.

3. A composition as claimed in claim 2 which has a viscosity between 0.6 and 250 centipoise at 37° C.

4. A composition as claimed in claim 1 wherein the resin is a urethane dimethacrylate resin or an epoxy dimethacrylate resin.

5. A composition as claimed in claim 1 further comprising a fluoride containing compound.

6. A polymerisable dental filling or sealing composition which comprises a mixture of a urethane dimethacrylate and/or a glycidyl methacrylate and at least about 40 wt % of a heterocyclic methacrylate to provide a polymerisable dental filling and sealing composition having a viscosity of less than 1340 centipoise at 37° C., and wherein the composition further comprises a tiller which is not reactive with the resin components.

7. A composition as claimed in claim 6 comprising THFMA, urethane dimethacrylate (UDMA) and bisphenol-A-glycidyl dimethacrylate (BisGMA) and having a viscosity between about 0.33 and 1340 centipoise at 37° C.

8. A composition as claimed in claim 6 wherein the heterocyclic methacrylate is THFMA.

9. A composition as claimed in claim 6 wherein the filler is flake glass.

10. A composition as claimed in claim 9 in which the flake glass has an average particle size between 0.5 and 10 μm.

11. A composition as claimed in claim 9 wherein the flake glass has an aspect ratio from about 5:1 to 10:1.

12. A composition as claimed in claim 1 comprising about 40 to 60 wt % THFMA; about 25 to about 35 wt % UDMA; and about 12 to about 18 wt % BisGMA.

13. A composition as claimed in claim 12 comprising about 50 wt % THFMA, about 33 wt % UDMA and about 16 wt % BisGMA.

14. A kit of parts for sealing a tooth cavity which comprises:
(a) a low viscosity sealant composition for infiltrating dentine in the cavity and partially filling the cavity, the sealant comprising at least one resin containing an average at least two acrylate or methacrylate groups and a copolymerisable methacrylate or acrylate monomer and having a viscosity of less than about 250 centipoise at 37° C.; and
(b) a reinforced bulk dentine substitute comprising tetrahydro-furfuryl methacrylate (THFMA), urethane dimethacrylate (UDMA) and bisphenol-A-glycidyl dimethacrylate (BisGMA) and a filler which is non-reactive with resin components at the composition, the dentine substitute having a viscosity of less than 1340 centipoise at 37° C.

15. A kit of parts as claimed in claim 14 wherein the resin comprises a urethane dimethacrylate or an epoxy dimethyacrylate.

16. A kit of parts according to claim 15 wherein the sealant composition is substantially free from filler.

17. A kit of parts according to claim 14 wherein the filler is flake glass.

18. A kit of parts as claimed in claim 17 wherein the flake glass has an average particle size of between 0.5 and 10 mm.

19. A kit of parts as claimed in claim 18 wherein the flake glass has an avenge aspect ratio of from about 5:1 to 10:1.

20. A kit of parts as claimed in claim 15 wherein the reinforced bulk dentine substitute comprises THFMA, UDMA and BisGMA in proportions of about 40 to 60 wt % THFMA; about 25 to about 35 wt % UDMA; and about 12 to about 18 wt % BisGMA.

21. A kit of parts as claimed in claim 14 wherein the reinforced bulk dentine substitute comprises THFMA, UDMA and BisGMA in proportions of about 50 wt % THFMA; about 33 wt % UDMA; and about 16 wt % BisGMA.

22. A composition as claimed in claim 1 wherein the resin is a urethane dimethacrylate or an epoxy dimethacrylate.

23. A composition as claimed in claim 1 wherein the filler is flake glass.

24. A composition as claimed in claim 23 wherein the flake glass has an average particle size of between 0.5 and 10 μm.

25. A composition as claimed in claim 23 wherein the flake glass has an aspect ratio of from 5:1 to about 10:1.

* * * * *